United States Patent [19]
Isaacs et al.

[11] Patent Number: 6,041,132
[45] Date of Patent: Mar. 21, 2000

[54] COMPUTED TOMOGRAPHY INSPECTION OF COMPOSITE PLY STRUCTURE

[75] Inventors: Ralph G. Isaacs, Cincinnati; Joseph M. Portaz, Hamilton, both of Ohio

[73] Assignee: General Electric Company, Cincinnati, Ohio

[21] Appl. No.: 08/902,565

[22] Filed: Jul. 29, 1997

[51] Int. Cl.[7] .................................. G06K 9/00; A61B 6/00
[52] U.S. Cl. ........................... 382/100; 378/21; 382/131; 382/293; 600/407
[58] Field of Search .................................. 382/128–134, 382/141, 148, 149, 154, 285, 196, 308, 100; 378/13–28, 4; 702/27; 345/423–424, 419, 420, 425; 364/474.31, 474.36; 600/410, 407; 348/130

[56] References Cited

U.S. PATENT DOCUMENTS

| | | | |
|---|---|---|---|
| 4,022,547 | 5/1977 | Stanley | 416/230 |
| 4,071,184 | 1/1978 | Carlson et al. | 228/559 |
| 4,284,896 | 8/1981 | Stonestrom | 378/14 |
| 4,670,840 | 6/1987 | Freundlich | 378/7 |
| 4,897,881 | 1/1990 | Ledinh et al. | 382/108 |
| 4,920,491 | 4/1990 | Eberhard et al. | 382/131 |
| 4,945,478 | 7/1990 | Merickel et al. | 382/131 |
| 4,949,282 | 8/1990 | Muraoka | 382/288 |
| 4,969,110 | 11/1990 | Little et al. | 382/131 |
| 4,984,157 | 1/1991 | Cline et al. | 345/424 |
| 5,023,895 | 6/1991 | McCroskey et al. | 378/21 |
| 5,027,378 | 6/1991 | Fujii et al. | 378/14 |
| 5,170,439 | 12/1992 | Zeng et al. | 382/131 |
| 5,185,809 | 2/1993 | Kennedy et al. | 382/131 |
| 5,222,202 | 6/1993 | Koyamada | 345/423 |
| 5,270,926 | 12/1993 | Tam | 378/4 |
| 5,297,043 | 3/1994 | Tuy et al. | 702/27 |
| 5,307,264 | 4/1994 | Waggener et al. | 378/14 |
| 5,331,552 | 7/1994 | Lloyd et al. | 378/15 |
| 5,345,514 | 9/1994 | Mahdavieh et al. | 382/152 |
| 5,351,078 | 9/1994 | Lemelson | 348/135 |
| 5,365,560 | 11/1994 | Tam | 378/14 |
| 5,375,156 | 12/1994 | Kuo-Petravic et al. | 378/9 |
| 5,375,978 | 12/1994 | Evans et al. | 416/230 |
| 5,396,528 | 3/1995 | Hu et al. | 378/14 |
| 5,430,788 | 7/1995 | Goto | 378/98.12 |
| 5,444,792 | 8/1995 | Grangeat et al. | 382/131 |
| 5,570,460 | 10/1996 | Ramanujam | 345/424 |
| 5,608,814 | 3/1997 | Gilmore et al. | 382/141 |
| 5,715,167 | 2/1998 | Gupta et al. | 364/474.28 |
| 5,795,295 | 8/1998 | Hellmuth et al. | 600/407 |

*Primary Examiner*—Jon Chang
*Assistant Examiner*—Jayanti K. Patel
*Attorney, Agent, or Firm*—Andrew C. Hess; Gerry S. Gressel

[57] ABSTRACT

A method of computed tomographic inspection which uses a Euclidian reference ply model having a corresponding Non-Euclidian ply model which includes reference model plies to extract intensity data from Euclidian slice data (typically having a pixel format) derived from multiple slice X-ray scans using an X-ray scanning system such as the CT system. The multiple slice data is analyzed to determine intensity values for points corresponding to a subject ply of a corresponding reference model ply. The reference model may be a predetermined model such as a mathematically described CAD model file or based on such a CAD model. A preferred method of the present invention includes a transformation of the CAD model data to register the CAD model data to multiple slice data of a standardized object to generate the reference model. Intensity values preferably gray scale pixel values are assigned to points on the reference ply model from the slice data and displayed as a Non-Euclidian image on a monitor.

20 Claims, 7 Drawing Sheets

COMPUTED TOMOGRAPHY INSPECTION OF COMPOSITE PLY STRUCTURE

BACKGROUND OF THE INVENTION

1. Field of the Invention

The present invention generally relates to the non-destructive computed tomography (CT) inspection of plies in composite materials and, in particular, a method for constructing a three-dimensional visualization of individual ones of such a ply using CT data.

2. Discussion of the Background Art

Over the years, the term composite has had several meanings regarding the use of two or more materials having different properties. More recently, in the aerospace industry, the term composite has come to be defined as a material containing a reinforcement such as fibers or particles supported in a binder or matrix material. Many composites may be used with the present invention including both metallic and non-metallic composites, however, the invention has a particular use with composites constructed with a unidirectional tape material and an epoxy resin matrix. A discussion of this and other suitable materials may be found in the "Engineering Materials Handbook" by ASM INTERNATIONAL, 1987–1989 or later editions, which are incorporated herein by reference. The composite blades and airfoils of the present invention are preferably of the non-metallic type made of a material containing a fiber such as a carbonaceous, silica, metal, metal oxide, or ceramic fiber embedded in a resin material such as Epoxy, PMR15, BMI, PEEU, etc. Of particular use are fibers unidirectionally aligned into a tape that is impregnated with a resin, formed into a part shape, and cured via an autoclaving process or press molding to form a light-weight, stiff, relatively homogeneous article having laminates within.

Composite materials are typically made by laying up or winding plies of material, injecting a resin into a container having the layed up material within, and then curing the resin. The process may produce anomalies such as waves or creases in some or all of the plies. Other types of so called "indications" are also of interest to composite manufacturers. It is therefore highly desirable to have techniques for investigating composites and displaying such indications in a manner by which the indications can be easily visualized. Such a visualization could be used for part conformance and particularly for inspections tests such as quality control on the assembly line or in the manufacturing process. Inspection using a non-destructive examination (NDE) method is best so as to minimize cost and time.

Computed tomography (CT) has long been a method for NDE inspection of metallic parts and human tissue. The high degree of homogeneity of composite parts poses a problem for inspection using CT apparatus and techniques. This is particularly true for indications, which tend to lie on ply surfaces. The problem is further exasperated when trying to inspect highly complex shapes such as composite fan blades of large gas turbine aircraft engines which have quite complex airfoil shapes. It is very difficult to determine the morphology or the extent of the indications.

CT systems, methods, and apparatus are well known in the art for inspecting large objects such as a gas turbine engine component, rocket engine component, or the like. They typically include a source of radiation and an associated detector both of which can be moved, relative to an object under inspection for purposes of reconstructing a cross-sectional area or slice through the object at a selected location on the object by means of penetrating the object with radiation and detecting the attenuation of the radiation caused by the object on an opposite side of the object from the radiation source. One X-ray inspection method and apparatus using Computed Tomography (CT) for which this invention was designed to be used with is explained in more detail in U.S. Pat. No. 5,119,408 which is incorporated herein by reference.

The present invention addresses the problems of NDE inspection of plies of composite parts using CT methods and, in particular, as applied to fan blades.

SUMMARY OF THE INVENTION

The present invention provides a non-destructive examination (NDE) computed tomography (CT) method for inspecting composite objects such as composite fan blades with a predetermined reference model ply from a predetermined reference ply model of at least a portion of the blade to guide a computerized marching algorithm to extract intensity data (grey scale pixel data) from multiple CT slices derived from multiple slice X-ray scans using an X-ray scanning system. The intensity data is used to generate a Non-Euclidian (2-D) image 100 of a single Euclidean (3-D) ply in the composite object which is capable of showing indications of interest such as wrinkles. A more specific embodiment is a computerized method for displaying an image of a subject ply of a subject object made of a composite material. This method uses the following steps: (a) generate and store a reference model of the subject object having at least one reference ply in a Non-Euclidian coordinate system; (b) three-dimensionally X-ray scan the subject object and use computed tomography (CT) to produce subject multiple slice data comprising subject CT slices that are substantially normal to actual plies of the subject object; (c) transform points of the reference ply to a Euclidian coordinate system of the subject object and register the points to the subject object; and (d) determine intensity values at transformed and registered points in the Euclidian coordinate system from at least some of the slice data in the vicinity of the transformed points. The transform step may include a transformation from a two-dimensional ply in the Non-Euclidian coordinate system to a three dimensional ply in the Euclidian coordinate system. The intensity values may be grey scale pixels and displayed on a computer monitor. The points may be equally spaced apart along the ply in the Non-Euclidian coordinate system and displayed in the Non-Euclidian coordinate system using an image display routine.

A more particular embodiment of the invention, particularly useful for production line NDE, is method wherein the reference model is based on a predetermined computerized model of the subject object and the transform step comprises a transformation that registers the predetermined computerized model to the subject object. This embodiment may further include registering the predetermined computerized model to a standard object, i.e. a first run part, to generate the reference model. Such a method may include a step (a1) performed before step (c) where step (a1) includes three-dimensionally X-ray scanning a standardized object that is related to the subject object and use computed tomography (CT) to produce standardized multiple slice data comprising CT slices that are substantially normal to actual plies of the standardized object. Step (c) includes a double transformation having a first transformation that registers the reference model to the standardized multiple slice data and a second transformation that registers the subject multiple slice data to the standardized multiple slice data. Subsequent NDE of subject parts would only then repeat the second transformation that registers the subject multiple slice data to the standardized multiple slice data.

ADVANTAGES

The present invention's major advantage is that it provides a reliable low cost method of non-destructive inspection of airfoil and other complex composite parts. A further advantage is that it can detect many indications that are otherwise very difficult to detect, classify and quantify. The method of the present invention provides a technique that should reduce operator error, and make classification of critical parts much easier, particularly for inspection of production parts and objects.

These features and advantages will become more readily apparent in the following description when taken in conjunction with the appended drawings.

BRIEF DESCRIPTION OF THE DRAWINGS

The invention, together with further objects and advantages thereof, is more particularly described in conjunction with the accompanying drawings in which.

DETAILED DESCRIPTION

Figure 1:
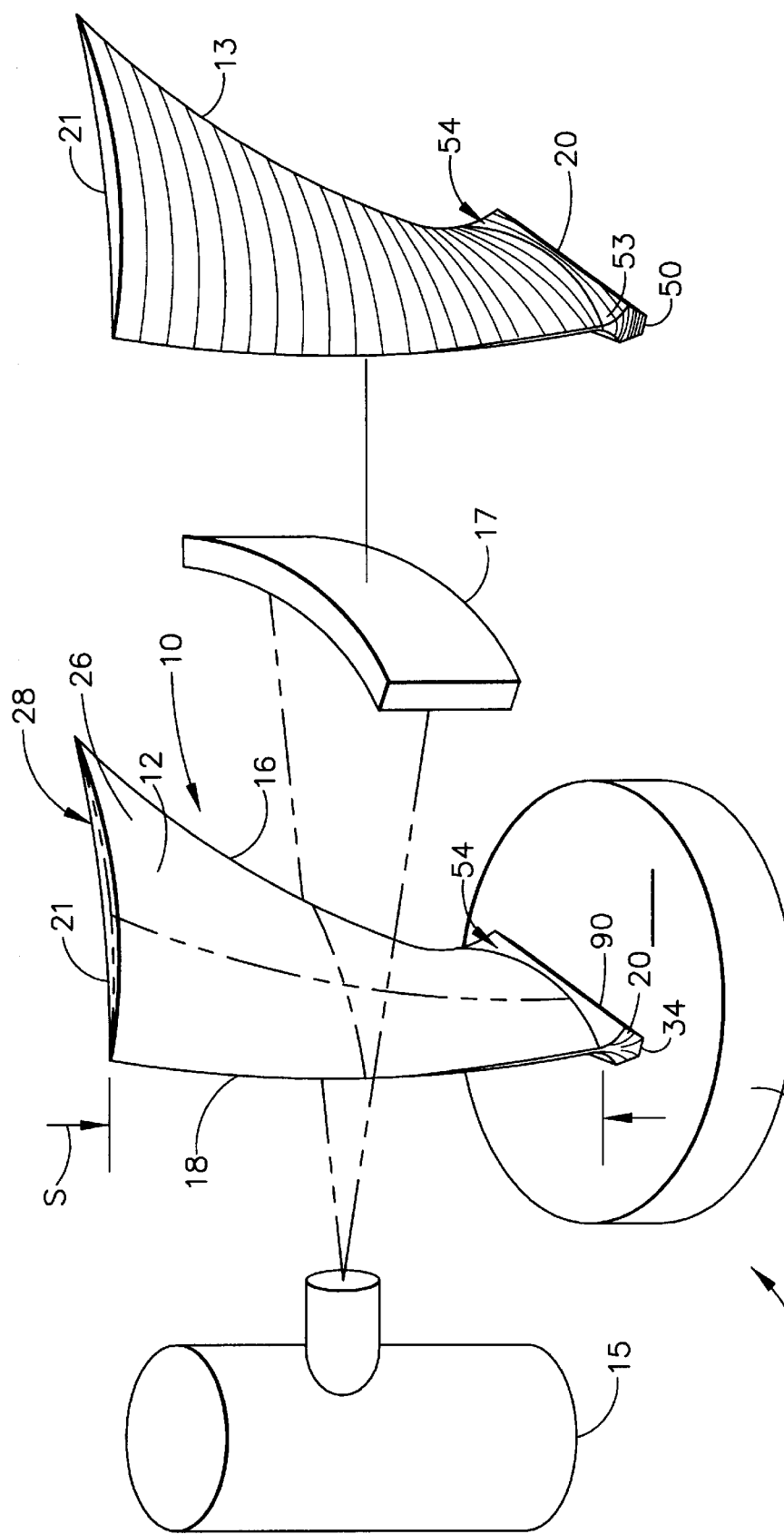
FIG. 1 is a diagrammatic flow chart illustrating the method of three-dimensionally X-ray scanning an exemplary composite object, a composite fan blade, to get CT slice data of the object.
Figure 2:
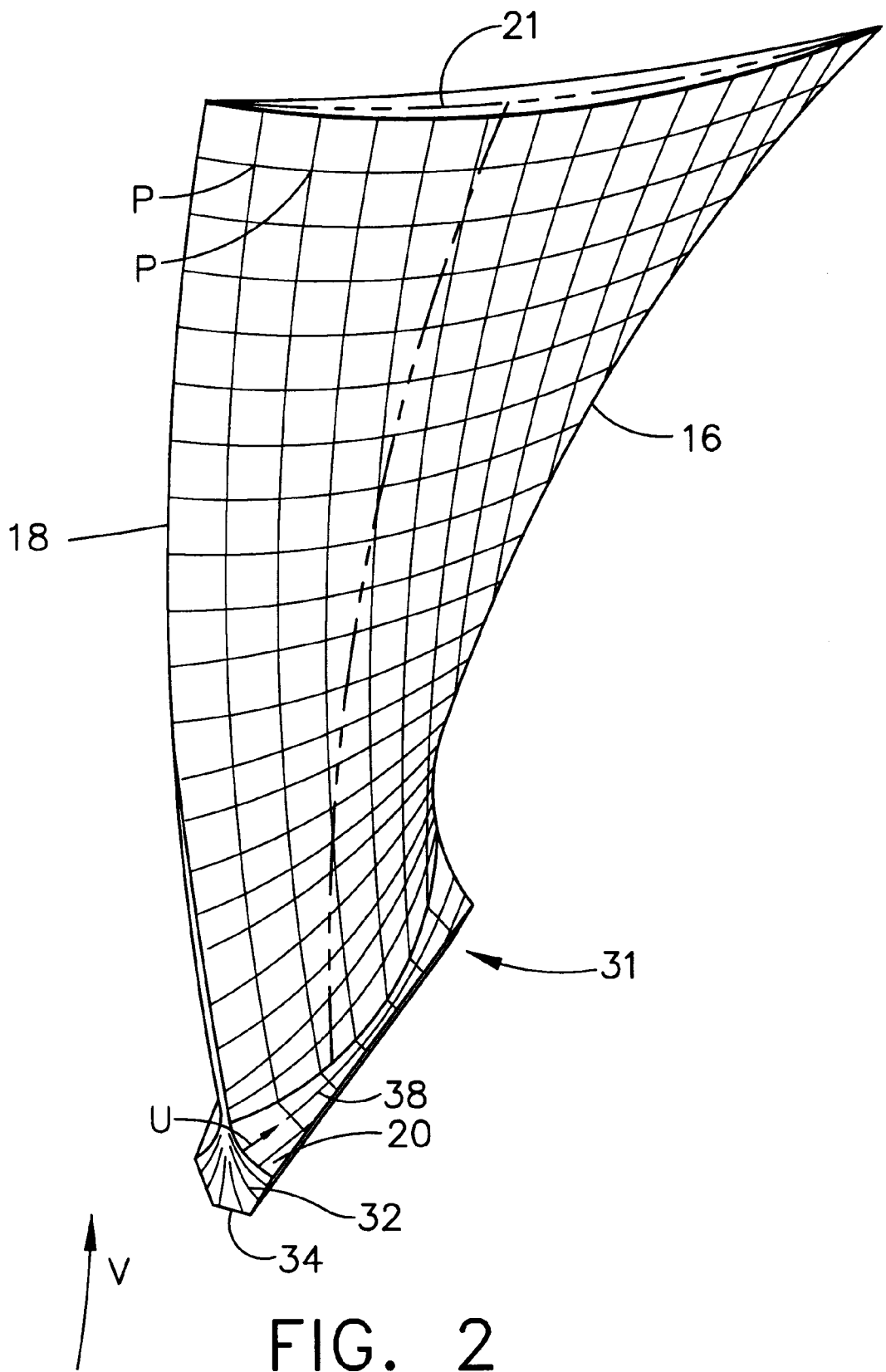
FIG. 2 is a diagram illustrating a CAD type predetermined reference ply model of the fan blade in FIG. 1.
Figure 5:
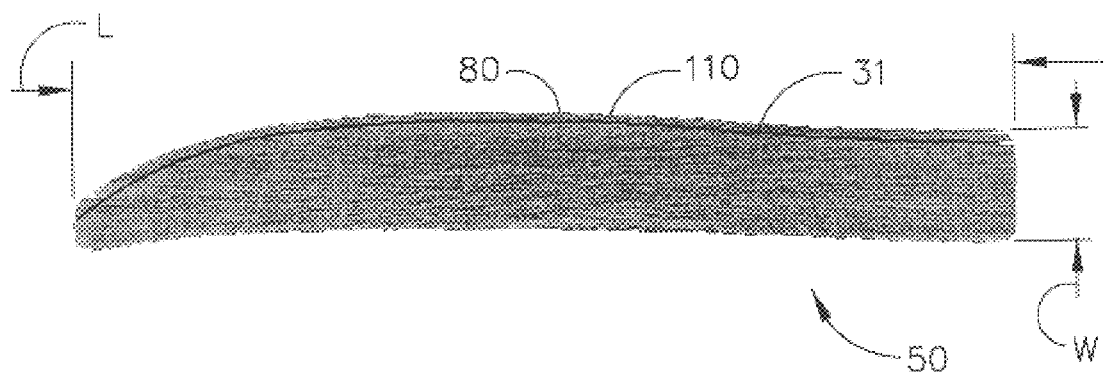
FIG. 5 is an image of a CT slice through the root of the blade in FIG. 1.
Figure 6:
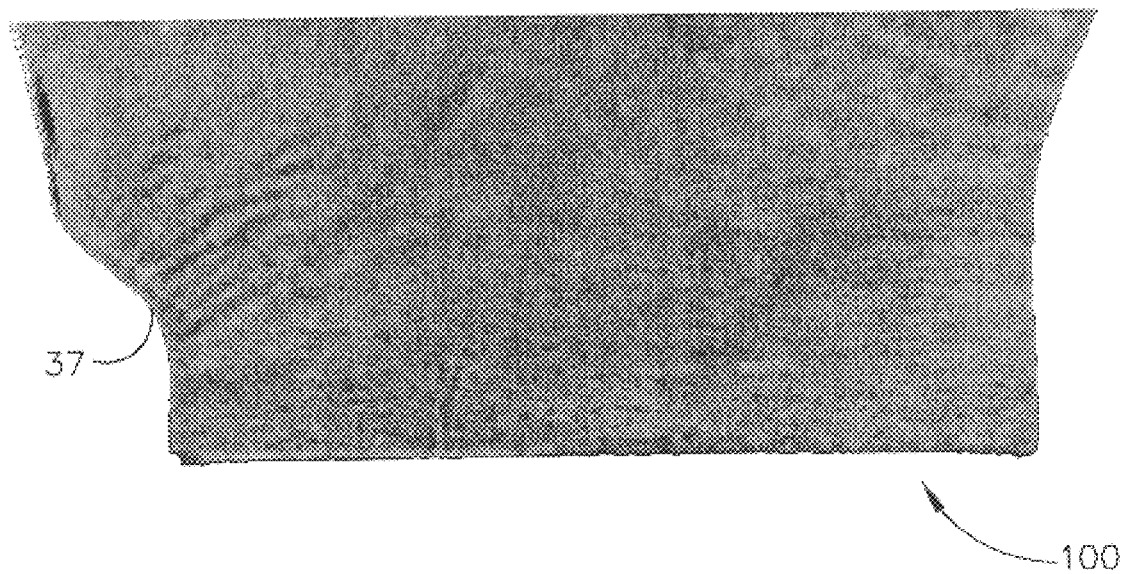
FIG. 6 is a CT ply image of a ply in the root of FIG. 1.

The present invention is an NDE CT method for inspecting composite objects such as a composite fan blade 10 illustrated in FIG. 1 by using a reference Euclidian model ply 32 (shown in greater detail in FIG. 3) which may be chosen from a predetermined reference ply model 31 of at least a portion of the blade as illustrated in FIG. 2, to guide a computerized marching algorithm to extract intensity data (gray scale pixel data) from multiple slice data 13 having multiple CT slices 50 such as a CT image illustrated in FIG. 5, derived from multiple slice X-ray scans using an X-ray scanning system such as the CT system 7. The intensity data is used to generate a Non-Euclidian image 100 of a single ply in the composite object which is capable of showing indications of interest such as wrinkles 37 as seen in FIG. 6.

Referring now in more detail to the drawings, there is schematically illustrated in FIG. 1 the composite fan blade 10 (which serves as an exemplary object to explain the method of the present invention) mounted in a manipulator 2 of a suitable X-ray computed tomography scanning system, hereinafter referred to as CT system 7, such as an industrial computed tomography system as described in U.S. Pat. No. 5,119,408. An X-ray source 15, such as a Philips MG model 450 420 kV high stability constant potential X-ray system, a Lintron 2 MeV source or the like, and an X-ray detector 17 such as a Xenon gas-type detector, solid state scintillator or the like are used to scan the object. Higher resolutions are possible by using known multiple sampling schemes. Detector elements (not shown) are preferably spaced in the linear array on centers of about 0.005 inches to about 0.04 inches apart to provide the high resolution. Suitable X-ray computed tomography scanning systems are well known in the art, an example being a GE Aircraft Engines' Industrial Computed Tomography System. The composite fan blade 10, designed for use in a high bypass ratio fanjet gas turbine engine (not shown), has a composite airfoil 12 typically including a leading edge 18 and a trailing edge 16. Composite airfoil 12 extends radially outward from a composite dovetail root 20 to tip 21, an extent generally defining its span S. Composite airfoil 12 has a convex side 26 and a concave side 28 and is made up of filament reinforced laminations or composite plies 30 formed from a composite material lay up as illustrated in FIG. 3.

Figure 4:
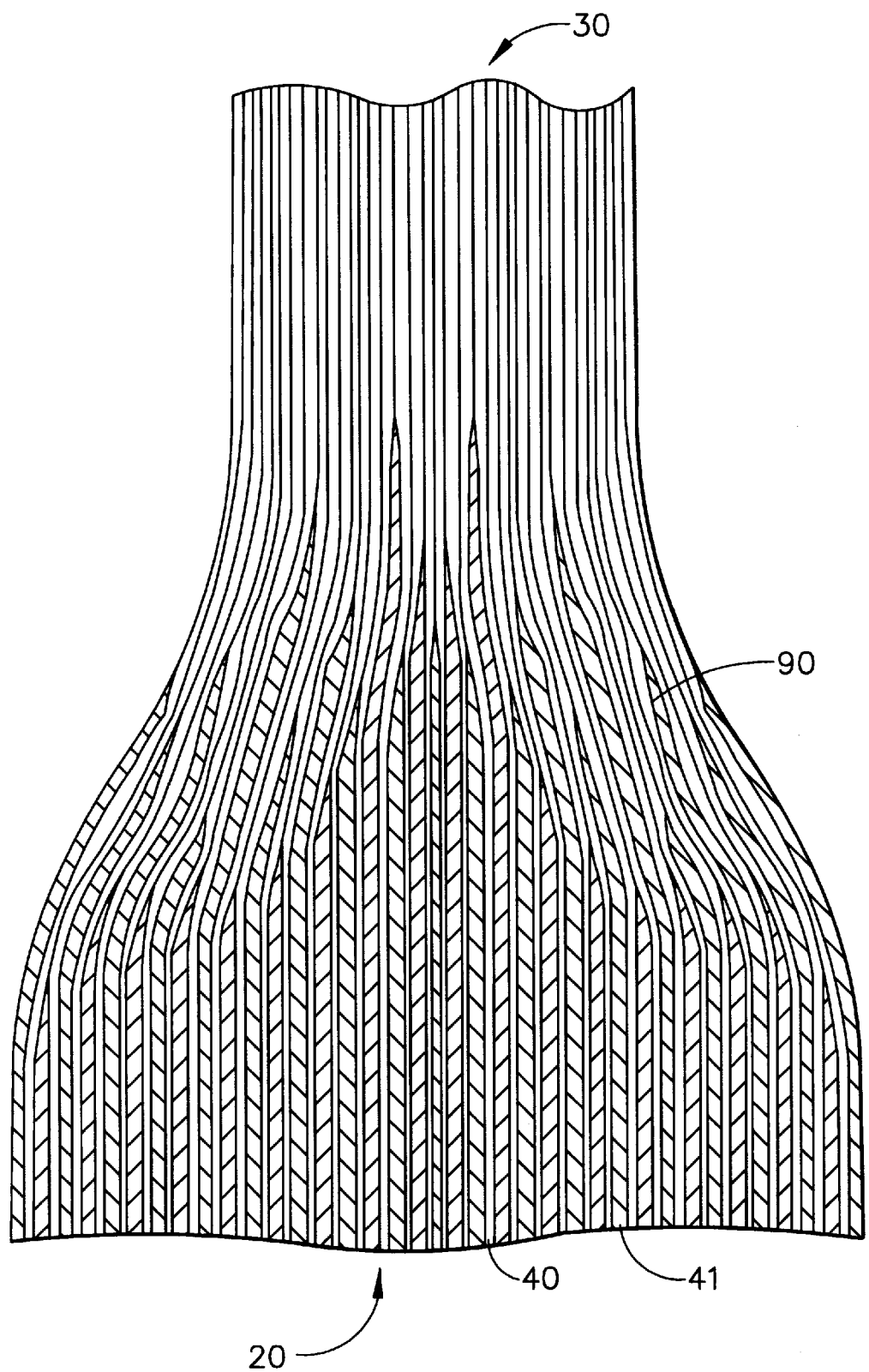
FIG. 4 is a cross-sectional illustration of a portion of a composite fan blade root similar to that of the blade in FIG. 1.

A portion of a ply lay-up 22 that is similar to but not having the same cross-sectional shape of the root 20 is illustrated in FIG. 4. The lay-up 22 has airfoil plies 40, indicated by white areas, and insert or dovetail plies 41, indicated by dark hatched areas, formed from unidirectional tape. The root 20, because of its complicated and complex curvature of it plies 30, is of particular interest and it is desirable to inspect the plies using an NDE method such as that of the present invention. The root 20 is scanned using CT system 7 to produce multiple slice data 13 having multiple CT slices 50 such as a CT image illustrated in FIG. 4.

The exemplary embodiment of the method uses a plurality of the CT slices 50, taken through the root 20, to generate a visual output such as the Non-Euclidian image 100 of a subject ply 90 of interest in the root. The reference model ply 32 in FIG. 3 is used to guide a computerized marching algorithm to extract intensity data from the slice data (typically having a pixel format) derived from multiple slice X-ray scans using an X-ray scanning system such as the CT system 7. The multiple slice data is analyzed to determine intensity values for Euclidian points P in the slice data corresponding to the subject ply 90 for which the corresponding reference model ply 32 has been selected.

Figure 3:
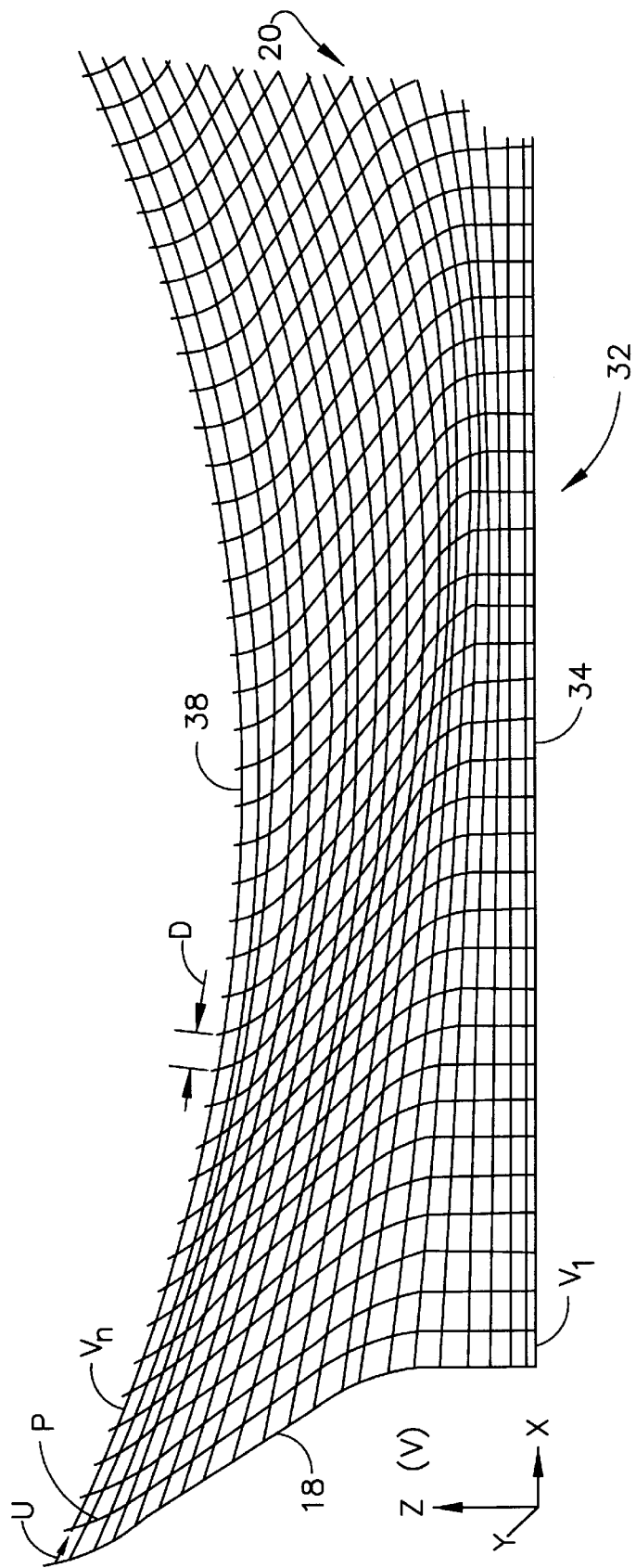
FIG. 3 is a single reference model ply from the ply reference model in FIG. 2.
Figure 7:
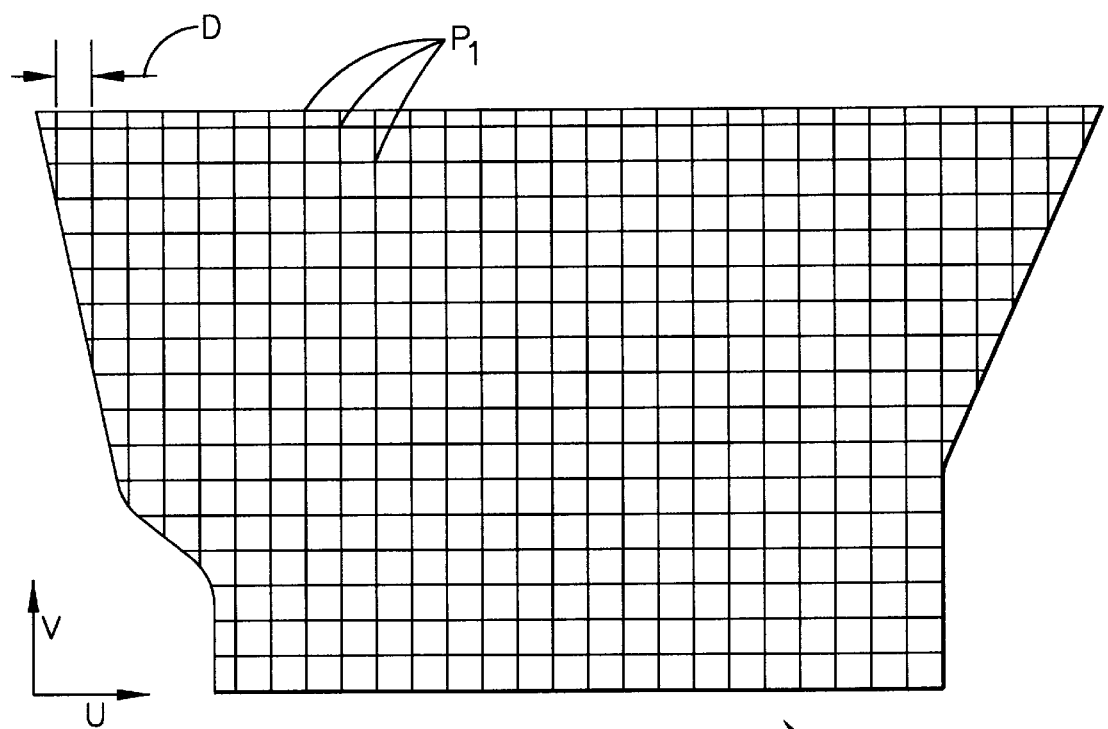
FIG. 7 is a diagrammatic representation of a Non-Euclidian display of a coordinate system of the reference model ply in FIG. 3.

Each model ply 32 is preferably stored as Euclidian points P in three-dimensional space having an x, y, and z coordinates (as illustrated in FIG. 3) for which there is a corresponding a flat array of Non-Euclidian points P' in the Non-Euclidian ply grid 33 (2-D model) illustrated in FIG. 7. The Non-Euclidian ply grid 33 has coordinates U and V where the coordinate U is the distance along a curved line 38 of reference model ply 32 (preferably measured from the trailing edge 16 of the blade and its model) along a constant height of the coordinate V as measured from a base 34 of the root 20. The Non-Euclidian ply grid 33 is illustrated as having a shape, leading edge 18, and trailing edge 16 that generally correspond to the planform shape of Euclidian model ply 32 such that U=0 is not a straight line parallel to the V axis but rather appears much like a side view of the Euclidian ply model. Though illustrated as having equally spaced apart curved lines 38, the parallel curved lines are preferably unequally spaced apart and may be more concentrated in areas corresponding to regions of the root that are more subject to anomalies such as where the actual plies are more curved.

Intensity or pixel values for Euclidian points P of at least one of the reference model plies are determined, preferably by Lagrangian interpolation from the slice data 13. The pixel values are then transformed to their corresponding Non-Euclidian points P' in the Non-Euclidian ply grid 33 for display as the Non-Euclidian image 100 by an image display routine on a monitor. The surface image such as the Non-Euclidian image 100 may be displayed using a standard commercially available package that can display 2D gray scale images such as PV-WAVE or IDL. PV-Wave is a data visualization tool available from Visual Numerics, 5105 East 41st Avenue, Denver Colo. 80216-9952. IDL is software for data visualization or image processing using 2D and 3D graphics and is available from Research Systems, Inc., 2995 Wilderness Place, Boulder, Colo. 80301. The image 100 clearly shows indications of interest such as wrinkles 37.

The subject object for which this inspection was developed are large composite fan blades. High energy X-rays, at least 420 KV, were used to image this part but the method of the present invention is not restricted to this type of part or X-ray energy. Because of the size and density of these parts, X-ray transmission can be less than 0.5% and yet the method is still effective. To reduce the effects of noise, highly efficient solid state detectors coupled to very quiet photodiode arrays were used. A technique referred to as bolusing is preferably used to overcome a problem with shallow angle scatter off the long surface of the airfoil. The problem is reduced by surrounding the object with a plastic or rubber like material having sufficient density to reduce the shallow angle scatter and which conforms tightly to the object. This is useful to reduce scatter artifacts. CT reconstruction of slice data 13 may be further enhanced by normalizing the X-ray projection data by subtracting offsets and multiplying by a gain vector and then applying a log operation to the data afterwards prior to CT reconstruction steps to generate the CT slices 50. Such techniques are well known and used by those skilled in the art.

A channel by channel beam hardening correction is also recommended for each view of X-ray data. For each channel, an inverse function to calculate thickness as a function of signal should be applied. The inverse functions are estimated by fitting measured data with a cubic polynomial as well as 3 truncated cubic polynomials. A singular value decomposition fit is suggested. A simple linear model for the detector, taking in account the detector aperture may be used to deconvolve cross-talk.

Other suggested CT reconstruction enhancement methods include fan beam reconstructions for both 360 degrees of data, and 180 plus fan angle reconstructions (using appropriate weighing factors as commonly know to those skilled in the art). The use of the method is not sensitive to the choice of reconstruction hardware or choice of kernel.

After CT reconstruction of the CT slices 50 it is suggested that two filtering steps be performed. A first one to remove ring artifacts and a second one to remove slowly varying "shading artifacts" caused by scatter and beam hardening. Both filters rely upon collecting historical data, for each slice height. This data has to be taken for each part type. Furthermore, when detectors or X-ray sources are changed or realigned, the historical data has to be retaken. Typically, the method should use data from 6 to 10 parts. Even if the parts have minor indications, there effects can be averaged out or eliminated. The filters themselves are images, either large subregions or as large as the CT image itself. The ring filter image is an estimate of the ring artifacts and is subtracted from the CT image. The shading filter is an image that multiplies the ring corrected CT image to reduce slowly varying shading artifacts.

Ring artifacts are present in CT images primarily because of differential non-linearities between adjacent detector channels. When X-ray penetration is very low, the channel by channel beam hardening correction does not remove these effects completely. The ring artifacts are estimated, by using high bypass filters along radii emanating from the center of reconstruction. The outputs from these filters are averaged and subtracted from subsequent images. There are several subtleties with this process. First, each of the historical images are registered with respect to a standard (a representative blade). This registration procedure is described below. Note, for ring filtering only rotations about the center of reconstruction are considered. Secondly, the ring filter is be applied only to pixels whose value is above a certain threshold to avoid applying it to air or the bolusing material. Thirdly, it is only applied to the interior of the blade, not the very edge. A simple morphological operator, i.e. a small radius ball, is used to detect whether most of the pixels are in the interior, i.e. above a threshold. Finally, the averaging of these estimates are done. Ring artifact correction is a method known in art as shown in U.S. Pat. No. 4,670,840 entitled "Ring Artifact Correction for Computerized Tomography".

Shading artifacts are estimated somewhat analogously. These artifacts are measured and corrected for after rings have been removed. The correction is multiplicative rather than additive (no correction is equivalent to multiplication by one). Since the shading artifacts move with the part reconstruction, all images coordinates are translated so that the COG's line up with the standards and are rotated, so that their moments line up with the standards. The filter value is extracted from the filter image (using bilinear interpolation) and the image pixel value is multiplied by the filter value.

To estimate the shading filter, one assumes the CT image is homogeneous and should have one X-ray absorption value. Small variations, including "stitches" and small indications, are averaged out in the process, or by using image processing techniques can be "morphed" out. The images are segmented using thresholding and morphological operations to make sure that only the interior of the blade (not the very edge) is used to develop the filters. For each image, a 3×3 low pass filter is applied to all pixels within the blade. The filter is adaptive in the sense that it only uses pixels that are within the blade. This average image is translated and rotated so that their COG's and moments are aligned with the standard. All these images are averaged and divided into an arbitrary standard value. Filter values for pixels not in the interior are set to 1.

Each filter has a header that describes its application (i.e. its size, its displacement, its application threshold, and its reference image's center of gravity (COG), as well as its moments and slice height). The reference image is a certain slice of a representative blade such as the standard blade described below. A CT slice 50 at a fairly high position 53 on a pressure face 54 of the dovetail root 20 is used to compute its COG using coordinates in pixel space weighted by the CT grey scale pixel value. Only pixels above a certain threshold value are used (so that only pixels in the part, not in the bolusing or air are used). The moments of inertia are computed in the same way, except the products of each pair of coordinates (e.g. xx, xy, yy) are weighted (less the COG coordinates) by the pixel value. The angle of the blade's principal axis, with to by the pixel value. The angle of the blade's principal axis, with the CT coordinate system, is computed by using:

$$\text{theta} = 0.5 * a\tan(2 * Ixy/(Ixx - Iyy))$$

Where Ixx and Iyy are the diagonal elements of the moment of inertia and Ixy is the off diagonal element. Note, that these are two-dimensional moments and COG's for a particular slice. However, the same transformation is used on all the slices as this was found to be practical and effective. If the fixturing had a tilt uncertainty, with respect to the staking lines of the blades, a corresponding full 3D transformation could be used.

To register a part which is either to be used in creating the ring and shading filters, the moments and COG of the standard slice is computed. A series of transformations, relating standard coordinates to particular image coordinates is developed. To transform an image into the standard coordinate system, we step through pixels in the standard coordinate system. The pixel coordinates are transformed to the part coordinates. Since these will in general be non-integral, a bilinear interpolation is used to calculate the pixel value. This method is used when calculating filter images.

The opposite is done when applying the filter. The method steps through the pixels of the part's CT slice 50 and transforms the part coordinates to the standard coordinates. Using bilinear interpolation filter values are extracted, which in turn are applied to the part's pixels. A final post processing step, median filtering images, has been found to be useful in preparing the images for surface reformatting.

The following is an illustration of a specific embodiment of the present invention for inspecting composite fan blades, the objects for which this invention was initially developed. The reference ply model 31 is derived from a predetermined mathematical CAD model in the form of a CAD file that relates Non-Euclidian coordinates for points of model plies 32 to Euclidean coordinates of a predetermined model. The Euclidean points P in the reference ply model are derived by registering the CAD model to a standard part or object. Registration of the CAD model to a standard composite blade is done by a transformation of an outside ply of the CAD reference model to the coordinate system of the CT slice data of the standard composite blade. This is then visually checked, as illustrated in FIG. 5, by observing agreement between a ply cross-section 110 and the shape of the edge or the contour of the CT slice 50. This is preferably done for various CT slices 50 along the blade which may include the airfoil as well as the root. An acceptable first production run composite fan blade found to be acceptable by various other methods of inspection, either of the non-destructive or destructive type may, for example, serve as the standard blade.

The surface model ply 32, for each ply of interest is registered, with respect to the standard blade. The Euclidean coordinates of each model ply 32, with respect to each slice of the standard blade or representative part is saved in a file. Registration information about the standard blade, such as center of gravity (COG) and moments of inertia (I), are also saved.

A set of X-ray Computed Tomographic CT slices 50 are taken using a linear detector or an area detector. With the linear detector, the slice spacing can be regular or can vary, depending on the variability and criticality of the regions. The registration information for this set of slices is compared to that of the standard blade and used to develop a transformation (presently a general linear one, but not restricted to this). The previously stored Euclidean points are transformed and used to make a multilinear interpolation of the volumetric multiple slice data 13. This step may be referred to as surface reformatting. This interpolation is made out of plane as well as in plane. The interpolated points are used to make images 100 of the subject plies of each production blade. The image 100 can be filtered such as with a median filter. It can be further processed by averaging it with images of neighboring plies or interpolating it with neighboring plies to look between the plies. Averaging four plies has been found to be beneficial in one case. The resultant images 100 are displayed and inspected visually, to detect indications. The images can also be inspected automatically or semi-automatically. Even though the image is that of a Non-Euclidian surface, tools are available to measure distances along the surface as well as the distance to the surface of the part. This can be done because the interpolating procedure can be reversed, i.e. we can go from the image, back to the Euclidean coordinates and the appropriate points on the nearest CT slice 50 or image.

Straightforward search or variation techniques can be used to compute geodesics (shortest distance paths) between points on the surface. The interpolated image also maintains the gray scale information of the original image. This is useful in determining the severity of the indication.

After the blades have been X-ray scanned, the volumetric CT slice data 13 should be reformatted to help analyze ply structure of composites and it can be looked at as two activities. The first, developing the reference ply model 31 is done once per part type and inspection technique. This relates each point P in 3D CAD Surface model coordinates to CT system coordinates. As long as the CAD model is valid then the number of CT slices 50, spacing D along the U coordinate of the plies, and the pixel size remain unchanged. This step has to be done only once a production run having a known standard blade or object. This is highly desirable because it is computationally expensive and time consuming. The output of this step is a set of triples (x, y, z coordinates), one for each Non-Euclidian points P' in the reformatted image 100 which are related to the Euclidian points P and the CT slices 50 and to particular pixels of CT slices. The output from this step is the reference ply model 31 and its model plies 32 each of which is stored in the computer.

One type of 3D CAD Surface model that has been used is a parametric model though non-parametric or implicit models may also be used. The 3D CAD Surface model uses 2 parameters U and V as shown in FIG. 7. V corresponds to the radial distance from the center of the engine and U corresponds to the Non-Euclidian distance from a point on the ply (of a fixed height or radius V) to the trailing edge 16. The distance D is Non-Euclidian because it is measured along the curved line 38 of the ply which is, of course, curved. A marching algorithm is used with a step along distance D of 0.5 mm increments in U and V. The V range in this exemplar illustration is limited to the dovetail root 20 area of the blade 10 for this exemplar illustration because it is of particular interest to composite fan blade manufacturers. Each one of the steps corresponds to a pixel size which is 0.5 mm×0.5 mm square (0.5 mm equals about 0.02 inches). A typical CT slice 50 has a root cross-section with a length L equal to about 12 inches and a width W of about 2.5 inches. Generating the reference model transforms the Euclidean 3D coordinates of the points P into Euclidian CT coordinates which are stored in the CT ply model 31 in a manner well known to those skilled in the art for use with a display routine to display the final image 100.

The first step of the transformation is of the Z coordinate for which in the CT coordinate system in FIG. 1, the z=0 plane corresponds to the first CT plane which is the closest CT slice 50 to the base 34 and is a simple linear translation. Next, the X and Y coordinates are translated and rotated, using the same vectors and 2D rotation matrix for all z. This method can be extended to a full 3D transformation, if for example the Z coordinates of the CAD model and the blade were skewed with respect to each other, however, it was not necessary for this application. This type of transformation is well known in the art. The transformations may be developed and checked by superimposing the CT ply model 31 Euclidian points P onto representative CT slices 50 as shown in FIG. 5 (for a root 20 cross-section). If the transformation matrix was wrong, the ply model would not follow the shape of the blade as illustrated by the edge 80 (airfoil and root cross-sections) for many or all of the CT slices 50 that are selected. By trial and error, the transformations may be quickly determined and confirmed visually by the superposition. One set of transformation may be used for all the plies.

The slice height and the center of gravity COG and the moments of inertia of a representative slice of the part used to develop the transformations are saved in a model header as is well known in the art. This is used to transform CT ply model coordinates to the coordinates of subject object or part to be inspected such as production composite blades.

Thus, for a ply model 31 x, y, z coordinates of a point P we use a simple transformation to convert the CAD model coordinates into reference coordinates x' and y'. The x, y coordinates are transformed to x' and y' by rotating them about the z axis as follows:

$$x'=\cos(theta)*x - \sin(theta)*y$$

$$y'=\sin(theta)*x + \cos(theta)*y$$

Then, the rotated coordinates are three-dimensionally translated to form reference coordinates x", y", and z", as follows:

$$x''=x'+delta\_x$$

$$y''=y'+delta\_y$$

$$z''=z'+delta\_z$$

Theta and delta_x, delta_y and delta_z are determined empirically, by looking at the intersection of the model with the part and making sure that the plies closest to the edge intersected close to the edge of the CT images 50 as described above. This is illustrated as the CT ply model 31 Euclidian points P on the representative CT slice 50 as shown in FIG. 5. These reference coordinates x", y", z" for each point P of each model ply 32 (registered to the standard blade) are stored in a file together with the header.

Figure 8:
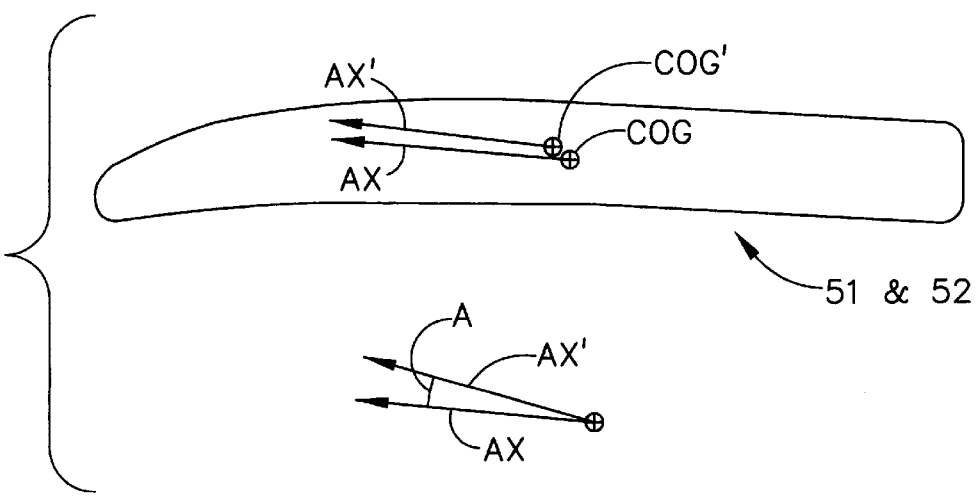
FIG. 8 is a diagram illustrating superimposed reference and production CT slices through the root of the blade in FIG. 1 and their respective COG's and principle axes.

FIG. 8 illustrates a representative slice 51 overlaid with a subject slice 52. The next step, which may be performed during production, is to transform the reference coordinates to production blade or subject object coordinates. The translation involves comparing a subject part's CT slice corresponding to the slice selected for reference part. More particularly a comparison is made of the subject center of gravity COG and subject moments of inertia Ixx and Iyy of a representative slice 51 of the production blade to the parameters reference part, i.e. a reference center of gravity COG' and reference moments of inertia Ixx' and Iyy' of the reference slice 51, at substantially the same radial coordinate Z. From this we develop a 2D translation (x,y) shown as the difference between the COG and the COG' and a 2D rotation shown as the angular difference A between a reference principle axis AX' and a subject principle axis AX. The reference principle axis AX' is derived from the reference moments of inertia Ixx' and Iyy' and the subject principle axis AX is derived from the subject moments of inertia Ixx and Iyy. The resultant transformed coordinates are used in the below discussed interpolation step.

Finally, as mentioned before, each step corresponds to a pixel saved in the reformatted image 100 as shown in FIGS. 6 and 7. To make the image more recognizable to an engineer or inspector, these pixels are imbedded in a rectangular matrix. The points corresponding to U=0, i.e. the trailing edge, are offset into the matrix, by an amount proportional to a plane that is tangent to a point high on the trailing edge. Secondly, the width of the matrix, is wide enough so that the leading edge is not clipped. The resultant image looks like a ply that is flattened out, but with a trailing and leading edge that looks recognizable.

Figure 9:
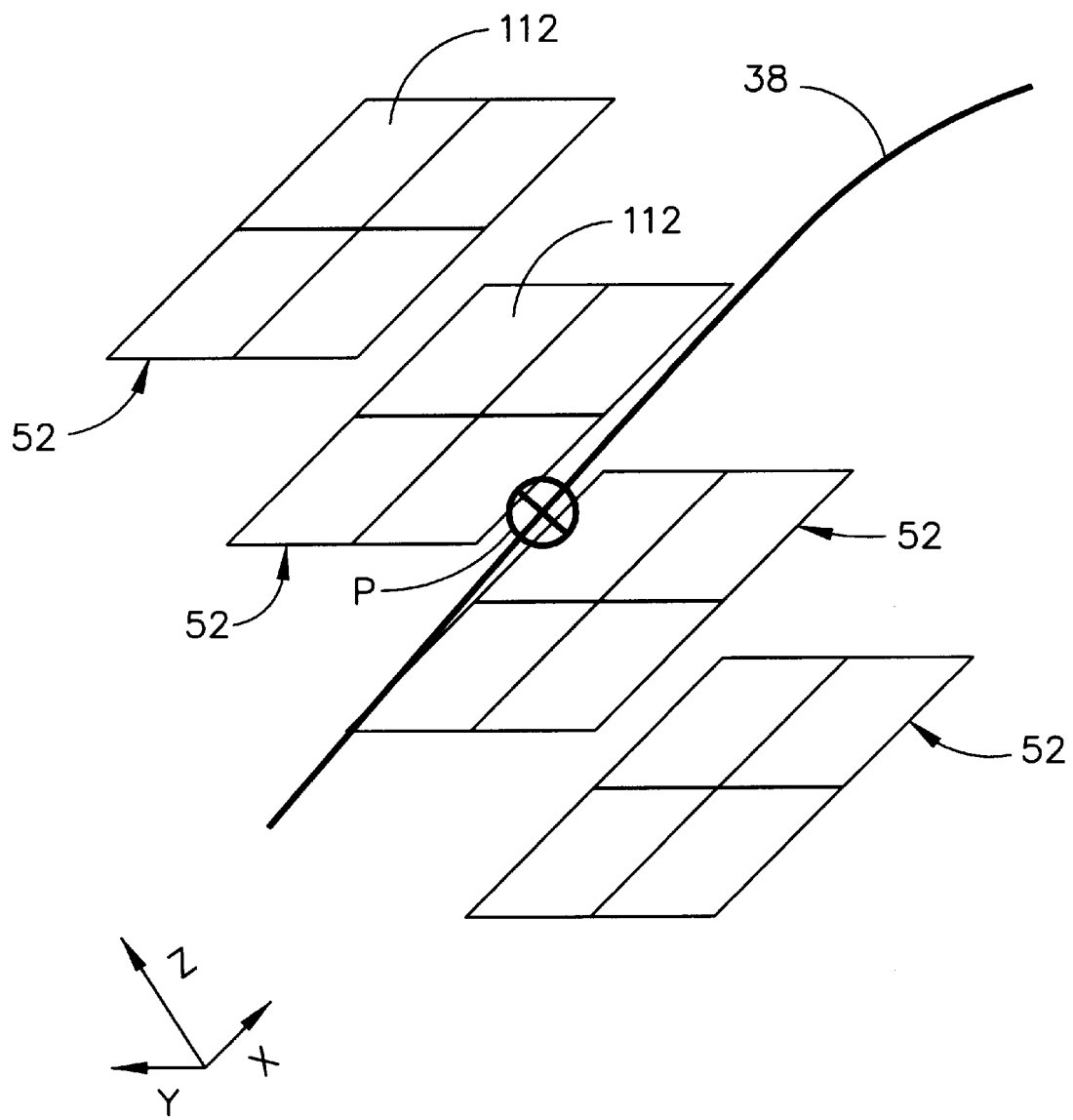
FIG. 9 is a diagrammatic perspective view illustrating a marching routine using Lagrangian interpolation for deriving pixel values at points P of the reference model from pixels of CT slices of the production fan blade in FIG. 1.

These coordinates are used to determine which slices are used to derive the pixel data for the image 100 and which pixels 112 in the slice is used during the marching routine along the curved lines 38 as illustrated in FIG. 9. A bilinear interpolation, using the nearest four points of each slice is used to determine intensity values for pixels in each slice used for each of the points in reference model ply from the pixels 112 of adjacent subject CT slices 52 of the blade. A Lagrangian interpolation of these results (four values, 1 for each of the four slices) in the V direction is used to obtain the intensity value, in pixel grey scale terms, for the point in the reference model.

For this particular application, 0.5 mm square pixels from the CT slice data 13 are used. However, the CT slice thickness and spacing may be variable, for example ranging from 1.5 mm to 3 mm with more critical areas get sampled more finely. A four point Lagrangian interpolation may be used for which the four nearest subject CT slices 52 (typically 2 above and 2 below) are used during the marching routines along the curve line 38 of the reference model in FIG. 3. Curved lines 38 of the reference model are preferably selected so that they do not lie exactly on a CT slice, i.e. there must be some interpolation. This is to avoid banding and any singularities. Finally, to reduce noise, the resultant image may be median filtered. Typically, a 3 by 3 median filter suffices.

The intensity or pixel data derived from the above steps is used to generate the Non-Euclidian image 100 of a single ply in the composite fan blade object which is capable of showing indications of interest such as wrinkles 37 as seen in FIG. 5.

The foregoing descriptive embodiments of the invention have been presented for the purpose of describing and illustrating the invention. It is not intended to be exhaustive or to limit the invention to the precise form disclosed and obviously many modifications and variations are possible in light of the above teachings. While the preferred embodiment of the invention has been described fully in order to explain its principles, it is understood that various modifications or alterations may be made to the preferred embodiment without departing from the scope of the invention as set forth in the appended claims.

What is claimed is:

1. A computerized method for displaying an image of a subject ply of a subject object made of a composite material, said method comprising the steps of:

(a) generate and store a reference model of a subject object made of a composite material having a plurality of actual plies, said reference model comprising at least one reference ply in a Non-Euclidian coordinate system and corresponding Euclidian coordinates;

(b) three-dimensionally X-ray scan the subject object and use computed tomography (CT) to produce subject multiple slice data comprising subject CT slices that are substantially normal to the actual plies of the subject object;

(c) transform points of the reference ply to a Euclidian coordinate system of the subject object and register the points to the subject object; and (d) determine intensity values of transformed and registered points in the Euclidian coordinate system from at least some of the slice data in the vicinity of the transformed points.

2. A method as claimed in claim 1 wherein the reference ply coincides with a Non-Euclidian axes of the Non-Euclidian coordinate system and the transform step comprises a transformation from a two-dimensional ply in the Non-Euclidian coordinate system to a ply in the three dimensional Euclidian coordinate system.

3. A method as claimed in claim 2 wherein the step to determine intensity values comprises an interpolation of intensity values of some of the slice data in the vicinity of the transformed points.

4. A method as claimed in claim 3 further comprises generating an image of the subject ply based on the intensity values.

5. A method as claimed in claim 4 wherein the points are equally spaced apart along the ply in the Non-Euclidian coordinate system.

6. A method as claimed in claim 5 wherein the image is displayed in the Non-Euclidian coordinate system.

7. A method as claimed in claim 6 wherein the image is displayed as a grey scale image.

8. A method as claimed in claim 4 wherein the reference model is based on a predetermined computerized model of the subject object and the transform step comprises a transformation that registers the predetermined computerized model to the subject object.

9. A computerized method for displaying an image of a subject ply of a subject object made of a composite material, said method comprising the steps of:

(a) generate and store a reference model of the subject object comprising at least one reference ply a Non-Euclidian coordinate system and corresponding Euclidian coordinates, wherein the reference ply coincides with a Non-Euclidian axes of the Non-Euclidian coordinate system and the reference model is based on a predetermined computerized model of the subject object;

(a1) three-dimensionally X-ray scanning a standardized object that is related to the subject object and use computed tomography (CT) to produce standardized multiple slice data comprising CT slices that are substantially normal to actual plies of the standardized object;

(b) three-dimensionally X-ray scan the subject object and use computed tomography (CT) to produce subject multiple slice data comprising subject CT slices that are substantially normal to actual plies of the subject object;

(c) transform points of the reference ply from a two-dimensional ply in the Non-Euclidian coordinate system to a three dimensional ply in the Euclidian coordinate system of the subject object and register points of the predetermined computerized model to the subject object wherein transforming points comprises a double transformation comprising a first transformation that registers the reference model to the standardized multiple slice data and a second transformation that registers the subject multiple slice data to the standardized multiple slice data;

(d) determine intensity values of transformed and registered points in the Euclidian coordinate system from at least some of the slice data in the vicinity of the transformed points by interpolating the intensity values of some of slice data in the vicinity of the transformed points;

(e) generating an image of the subject ply based on the intensity values.

10. A method as claimed in claim 9 wherein said step (a1) and said first transformation are done once and a plurality of subject objects are examined using one of said second transformation for subject multiple slice data for each of said plurality of subject objects to display image of subject plies.

11. A method as claimed in claim 10 wherein the points are equally spaced apart along the ply in the Non-Euclidian coordinate system.

12. A method as claimed in claim 11 wherein the image is displayed in the Non-Euclidian coordinate system.

13. A method as claimed in claim 12 wherein the image is displayed as a grey scale image.

14. A computerized method for displaying images of a plurality of subject plies of subject composite fan blades, said method comprising the steps of:

(a1) three-dimensionally X-ray scanning a standard fan blade that is related to the subject fan blades and use computed tomography (CT) to produce standardized multiple slice data comprising CT slices that are substantially normal to actual plies of the standard fan blade;

(a2) generate and store a predetermined ply model of the fan blade comprising a plurality of predetermined plies in a Non-Euclidian coordinate system and corresponding Euclidian coordinates;

(a) generate and store a reference model of the fan blade comprising a plurality of reference plies in a Non-Euclidian coordinate system and corresponding Euclidian coordinates by a first transformation that registers the predetermined ply model to the standardized multiple slice data;

(b) three-dimensionally X-ray scan a subject fan blade and use computed tomography (CT) to produce subject fan blade multiple slice data comprising subject CT slices that are substantially normal to actual plies of the subject fan blade;

(c) use a second transformation to transform points of one of the reference plies to a Euclidian coordinate system of the subject fan blade and register the points to the subject fan blade; and (d) determine intensity values of transformed and registered points in the Euclidian coordinate system of the subject fan blade from at least some of the slice data in the vicinity of the transformed points.

15. A method as claimed in claim 14 wherein;

the reference ply coincides with a Non-Euclidian axes of the Non-Euclidian coordinate system, the first transformation is from a two-dimensional ply in the Non-Euclidian coordinate system to a ply in the three dimensional Euclidian coordinate system of the standardized fan blade, and the method further comprises generating an image of the subject ply based on the intensity values.

16. A method as claimed in claim 15 wherein the step to determine intensity values comprises an interpolation of intensity values of some of the slice data in the vicinity of the transformed points.

17. A method as claimed in claim 16 wherein the predetermined model is a mathematical CAD model in the form of a CAD file.

18. A method as claimed in claim 17 wherein said steps (b) through (d) are repeated for multiple subject fan blades using the same reference model of the fan blade and reference plies from step (a).

19. A method as claimed in claim 18 wherein the points are equally spaced apart along the ply in the Non-Euclidian coordinate system.

20. A method as claimed in claim 19 wherein the image is displayed in the Non-Euclidian coordinate system as a grey scale image.

* * * * *